US010046325B2

(12) United States Patent
Beckerdite et al.

(10) Patent No.: US 10,046,325 B2
(45) Date of Patent: Aug. 14, 2018

(54) SELF-HEATING DEVICE FOR WARMING OF BIOLOGICAL SAMPLES

(71) Applicant: Rechargeable Battery Corporation, College Station, TX (US)

(72) Inventors: John Beckerdite, College Station, TX (US); Christopher Pedicini, Franklin, TN (US)

(73) Assignee: RECHARGEABLE BATTERY CORPORATION, College Station, TX (US)

( * ) Notice: Subject to any disclaimer, the term of this patent is extended or adjusted under 35 U.S.C. 154(b) by 0 days.

(21) Appl. No.: 14/670,704

(22) Filed: Mar. 27, 2015

(65) Prior Publication Data
US 2016/0279638 A1 Sep. 29, 2016

(51) Int. Cl.
*B01L 7/00* (2006.01)
*B01L 7/02* (2006.01)
*G01N 1/44* (2006.01)

(52) U.S. Cl.
CPC .............. *B01L 7/00* (2013.01); *G01N 1/44* (2013.01); *B01L 7/02* (2013.01); *B01L 2200/147* (2013.01); *B01L 2300/1855* (2013.01)

(58) Field of Classification Search
CPC .............. B01L 2300/1855; B01L 7/00; B01L 2200/147; B01L 7/02; B01L 3/508; G01N 1/28; B01D 3/06; B01D 53/48; B01D 53/62; B01J 19/0093; B01J 19/24; B01J 2219/00864; B01J 2219/00867; B01J 2219/00871; B01J 2/00
See application file for complete search history.

(56) References Cited

U.S. PATENT DOCUMENTS

| | | |
|---|---|---|
| 1,216,816 A | 2/1917 | Kincaid |
| 2,261,221 A | 11/1941 | Bruner |
| 2,533,958 A | 12/1950 | Root et al. |
| 2,573,791 A | 11/1951 | Howells |
| 2,589,645 A | 3/1952 | Tiegel |
| 3,064,640 A | 11/1962 | Donath |
| 3,261,347 A | 7/1966 | Sherman |
| 3,301,250 A | 1/1967 | Glasser |
| 3,774,589 A | 11/1973 | Kober |
| 3,976,049 A | 8/1976 | Yamashita et al. |
| 4,093,424 A | 6/1978 | Yoshida et al. |
| 4,106,478 A | 8/1978 | Higashijima |
| 4,114,591 A | 9/1978 | Nakagawa |
| 4,205,957 A | 6/1980 | Fujiwara |
| 4,255,157 A | 3/1981 | Yamaguchi et al. |
| 4,282,005 A | 8/1981 | Sato et al. |
| 4,366,804 A | 1/1983 | Abe |
| 4,516,564 A | 5/1985 | Koiso et al. |
| 4,522,190 A | 6/1985 | Kuhn et al. |
| 4,545,362 A | 10/1985 | Hendricks |
| RE32,026 E | 11/1985 | Yamashita et al. |
| 4,664,674 A | 5/1987 | Oftedal et al. |
| 4,756,299 A | 7/1988 | Podella |
| 4,901,472 A | 2/1990 | Donohue et al. |
| 4,995,126 A | 2/1991 | Matsuda |
| 5,042,455 A | 8/1991 | Yue et al. |
| 5,046,479 A | 9/1991 | Usui |
| 5,117,809 A | 6/1992 | Scaringe et al. |
| 5,125,392 A | 6/1992 | Hardwick |
| 5,606,144 A | 2/1997 | Simmons et al. |
| 5,635,397 A | 6/1997 | Futschik et al. |
| 5,873,254 A | 2/1999 | Arav |
| 5,879,378 A | 3/1999 | Usui |
| 5,915,373 A | 6/1999 | Malover et al. |
| 5,918,590 A | 7/1999 | Burkett et al. |
| 5,975,074 A | 11/1999 | Koiso et al. |
| 5,984,953 A | 11/1999 | Sabin et al. |
| 5,984,995 A | 11/1999 | White |
| 6,020,040 A | 2/2000 | Cramer et al. |
| 6,099,556 A | 8/2000 | Usui |
| 6,436,128 B1 | 8/2002 | Usui |
| 6,886,553 B2 | 5/2005 | Yim |
| 6,915,798 B2 | 7/2005 | Minami |
| 7,041,123 B2 | 5/2006 | Stapf et al. |
| 7,234,458 B2 | 6/2007 | Takeuchi et al. |
| 7,611,767 B2 | 11/2009 | Usui et al. |
| 7,621,110 B2 | 11/2009 | Ota et al. |
| 7,722,782 B2 | 5/2010 | Coffey et al. |
| 7,749,357 B2 | 7/2010 | Kumamoto et al. |
| 7,878,187 B2 | 2/2011 | York-Leung Wong |
| 7,950,385 B2 | 5/2011 | Obnishi et al. |
| 8,256,412 B2 | 9/2012 | Kumamoto et al. |
| 8,261,734 B2 | 9/2012 | Dodo |
| 8,431,387 B2 | 4/2013 | Labarre et al. |

(Continued)

FOREIGN PATENT DOCUMENTS

WO 83/01994 A1 6/1983
WO 2016/164540 10/2016

OTHER PUBLICATIONS

Gudheim, "The Specific and Latent Heats of Fusion of Some Veg. Fats and Oils", Oil and Soap, May 1944, pp. 129-133.*

(Continued)

*Primary Examiner* — Debbie K Ware
(74) *Attorney, Agent, or Firm* — Schroeder Intellectual Property Law Group, LLC

(57) ABSTRACT

A method and device for warming biological samples utilizes a heater and an outer chamber fabricated from a thermal regulating material. The outer chamber includes an outer surface and an inner surface with the heater being in operative contact with at least a portion of the outer surface of the outer chamber. A biological sample receiving region defined by the inner surface of the outer chamber is included, the biological receiving region being configured to operatively accept a biological sample and, alternatively including a liquid that has a freezing point near to or below that of the biological sample, and, wherein one or more of the inner surface and the liquid is in close and intimate contact with the biological sample. The thermal regulating material may obtain and maintain a substantially constant predetermined temperature when heat is imparted to the outer chamber by the heater.

20 Claims, 4 Drawing Sheets

(56) References Cited

U.S. PATENT DOCUMENTS

| | | |
|---|---|---|
| 9,004,059 B2 | 4/2015 | Sesock et al. |
| 9,024,360 B1 | 5/2015 | Huffer et al. |
| 9,278,796 B2 | 3/2016 | Huffer et al. |
| 9,642,736 B2 | 5/2017 | Laubach et al. |
| 9,872,795 B2 | 1/2018 | Laubach et al. |
| 2001/0037872 A1 | 11/2001 | Sabin et al. |
| 2002/0020406 A1 | 2/2002 | Minami |
| 2002/0092517 A1 | 7/2002 | Jelten |
| 2004/0261783 A1 | 12/2004 | Madan et al. |
| 2005/0028806 A1 | 2/2005 | Kumamoto et al. |
| 2005/0172951 A1 | 8/2005 | Yim |
| 2007/0000484 A1 | 1/2007 | Magill et al. |
| 2007/0006870 A1 | 1/2007 | Danforth |
| 2007/0256677 A1 | 11/2007 | Yim et al. |
| 2007/0256678 A1 | 11/2007 | Yim et al. |
| 2007/0256679 A1 | 11/2007 | Yim et al. |
| 2007/0261692 A1 | 11/2007 | Bolmer et al. |
| 2007/0277806 A1 | 12/2007 | Dodo |
| 2008/0029080 A1 | 2/2008 | Dodo |
| 2008/0082151 A1 | 4/2008 | Quincy et al. |
| 2008/0087271 A1 | 4/2008 | Ajiri et al. |
| 2008/0169355 A1 | 7/2008 | Pohl et al. |
| 2008/0245358 A1 | 10/2008 | Bolmer et al. |
| 2008/0251062 A1 | 10/2008 | Dodo |
| 2009/0007899 A1 | 1/2009 | Dodo |
| 2010/0089381 A1 | 4/2010 | Bolmer et al. |
| 2010/0163011 A1 | 7/2010 | Tinker et al. |
| 2010/0279299 A1 | 11/2010 | Maltezos et al. |
| 2011/0073099 A1 | 3/2011 | Madan et al. |
| 2011/0126821 A1 | 6/2011 | Wilson et al. |
| 2013/0174835 A1 | 7/2013 | Tinker et al. |
| 2014/0008042 A1 | 1/2014 | Schryver et al. |
| 2014/0102435 A1 | 4/2014 | Sesock et al. |
| 2014/0109889 A1 | 4/2014 | Pedicini et al. |
| 2014/0109890 A1 | 4/2014 | Pedicini et al. |
| 2015/0059729 A1 | 3/2015 | Tinker et al. |
| 2016/0161149 A1 | 6/2016 | Laubach et al. |

OTHER PUBLICATIONS

International Search Report and Written Opinion dated Jun. 16, 2016 for related International Application No. PCT/US2016/023697, 12 pages.

Unpublished U.S. Appl. No. 15/589,190, filed May 8, 2017.

Unpublished U.S. Appl. No. 15/875,094, filed Jan. 19, 2018.

Unpublished U.S. Appl. No. 15/564,460, filed Oct. 5, 2017, originally filed Apr. 7, 2016 and published as WO 2016/164540.

\* cited by examiner

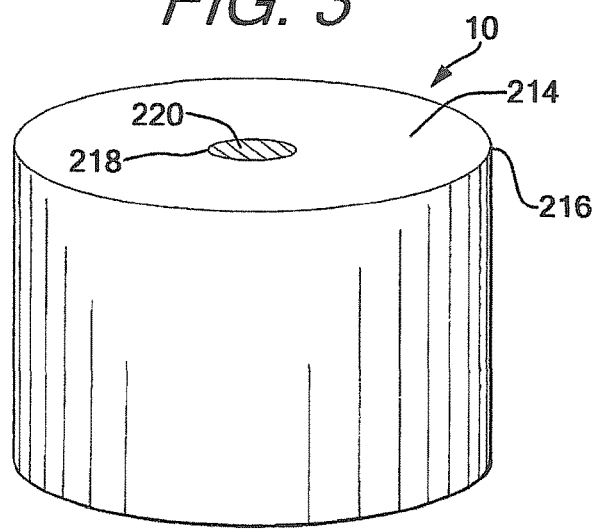
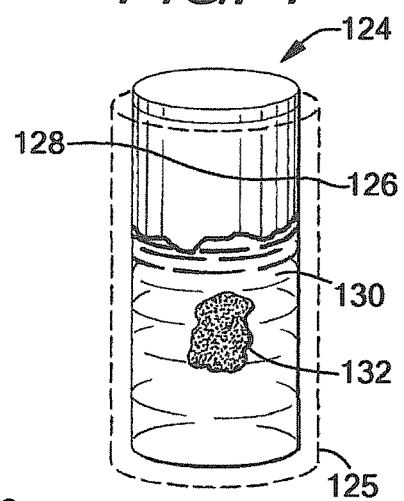
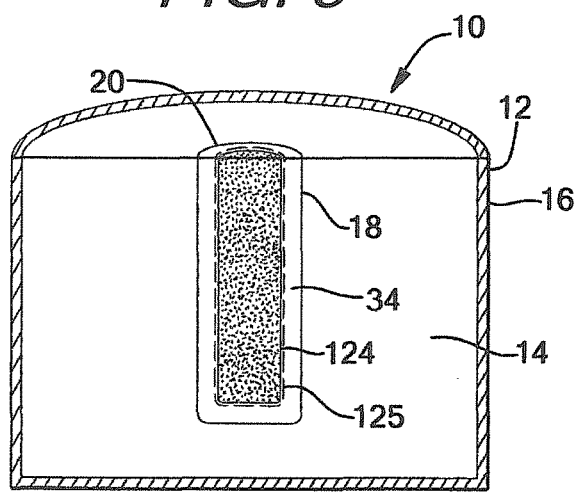

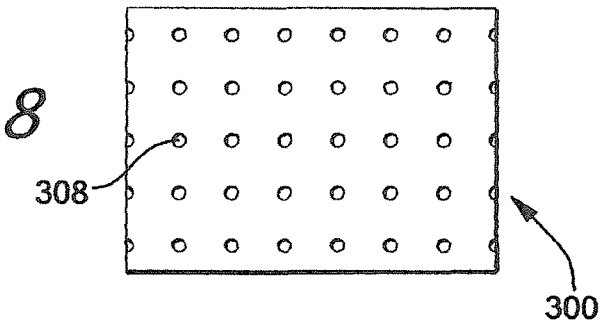
FIG. 8
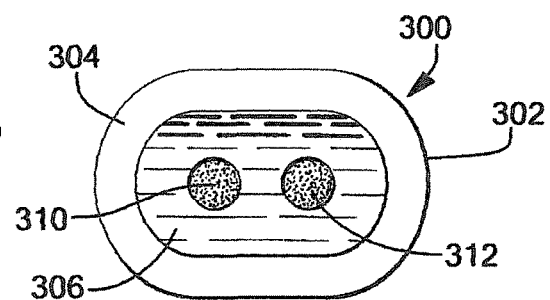
FIG. 9
FIG. 10
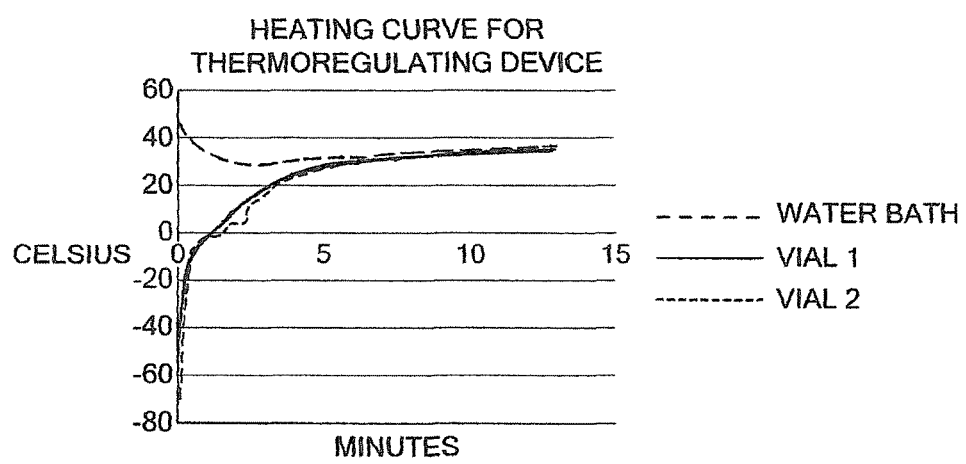

SELF-HEATING DEVICE FOR WARMING OF BIOLOGICAL SAMPLES

CROSS REFERENCE TO RELATED APPLICATIONS

None.

FIELD OF THE INVENTION

The invention relates to a warming device for the uniform heating of preserved biological samples, and doing so while controlling the maximum temperature the samples are exposed to.

BACKGROUND OF THE INVENTION

Many live-cell containing samples and systems are frozen and stored at low temperature, (e.g., −80° C.) with the intent that the samples will be thawed for later use. Cryoprotectants such as glycerin are often added to the freezing solution in order to minimize damage related to ice and ice crystal formation. Rapid freezing may further prevent ice crystal formation, however it may induce severe stress on the samples.

When thawing live-cell containing samples and systems, it is desirable to warm the sample quickly while at the same time minimizing the temperature excursions that could otherwise negatively impact cell viability. Presently, frozen biological samples are frequently warmed in a water bath having a temperature ranging from 20° C. to 60° C. The primary challenge associated with water baths is that water baths tend to have a lack of portability, and are generally unable to quickly change and equilibrate at a desired temperature.

Therefore, there is a need for a portable warming device that is able to quickly and uniformly heat frozen biological samples while being maintained at a desired temperature or within a desired temperature range. The present invention is provided to solve these and other problems.

SUMMARY OF THE INVENTION

The present invention is directed to a device and method for warming biological samples at a substantially constant temperature well below what will damage the biological sample once warmed.

According to one aspect of the invention, the device includes a heater and an outer chamber fabricated from a thermal regulating material. The outer chamber includes an outer surface and an inner surface. The heater may operatively contact or be operatively coupled with at least a portion of the outer surface of the outer chamber in order to impart heat on the outer chamber. The device further includes a biological sample receiving region or biological receiving region or receiving region defined by the inner surface of the outer chamber. The biological sample receiving region may be configured to operatively accept a biological sample, frozen or otherwise, either directly or in a container. The biological sample may optionally be surrounded and placed in intimate contact with a liquid contained in the biological sample receiving region. It may be desired to select a liquid with a freezing point near to or below that of the temperature of the biological sample. Once the heater is activated, the thermal regulating material will obtain and maintain a substantially constant predetermined temperature subsequent to heat being imparted to the outer chamber. Notwithstanding the foregoing, it is contemplated that the heater is integrally associated with the outer surface of the outer chamber, such as by chemical or mechanical adhesion thereto, or, that the heater is a separate component that is subsequently mechanically coupled with the outer chamber—as would be understood to those with ordinary skill in the art.

According to another aspect of the invention, the thermal regulating material may be a solid material that undergoes a phase change to a liquid state upon exposure to a predetermined temperature imparted to it from the heater. The temperature of the thermal regulating material will remain substantially constant due to its latent heat of fusion while the heat imparted to it from the heater causes the phase change from its solid state to its liquid state, until the phase change is complete and the entire thermal regulating material is liquefied. As it melts, the thermal regulating device will transfer heat to the liquid surrounding and in intimate contact with the biological sample. The heat provided to the biological sample should be a temperature that will thaw and/or warm the biological sample without causing damage thereto, i.e. being too high or over a threshold which may damage the sample. After the heating step is completed the latent heat of fusion of the thermal capacitor again may come into play as the thermal capacitor material re-solidifies. If the liquid surrounding the biological sample remains at a lower temperature than the temperature of the melted or partially-melted thermal capacitor, then the heat released by the solidification process of the thermal capacitor can continue to warm the liquid surrounding and in intimate contact with the biological sample, and hence, continue to warm the biological sample itself. An example of a thermal regulating material can be found in Applicant's co-pending U.S. Pat. Pub. No. 2014/0109889, the entirety of which is incorporated herein by reference.

According to another aspect of the invention, the device may include a container, which may be removable, positioned within the biological sample receiving region. The container having an outer surface, at least a portion of which will be surrounded by and in operative contact with the inner surface of the outer chamber. The container will also have an inner surface, and, an interior region for operative positioning of the biological sample and any liquid used to surround and be in intimate contact with the biological sample. The container may be fabricated from a material that allows for effective heat transfer from the thermal regulating material so as to enable heating, and, in turn, thawing or warming of the biological sample without causing damage thereto, like for example, a glass or plastic vial. The device may further include a sleeve capable of surrounding and isolating the container from the thermal regulating material or any liquid surrounding the container.

According to another aspect of the invention, the heater comprises a heater that produces heat from an exothermic reaction. The heater may be, for example, an oxygen activated heater like that taught in Applicant's co-pending U. S. Pat. Pub. nos. 2014/0109889, 2014/0102435, and 2013/0174835 (the entirety of which are incorporated herein by reference).

According to another aspect of the invention, the thermal regulating material may be fabricated from, for example, palm oil, palm kernel oil, coconut oil, hydrogenated palm oil, hydrogenated palm kernel oil, hydrogenated coconut oil, hydrogenated soybean oil, hydrogenated cottonseed oil, a distearate of polyethylene glycol, or combinations thereof. The thermal regulating material may also include 1-hexadecanol. Regardless of the material used to form the thermal regulating material, the thermal regulating material should have a melting point of approximately 37° C., and should have a latent heat of at least 20 cal/g. More preferably, the thermal regulating material will have a latent heat of at least 30 cal/g, or even more preferably, of at least 40 cal/g.

According to one aspect of the invention, a method for uniformly heating a biological sample is provided. A heater is engaged with an outer surface of a device having an outer chamber and an inner chamber defined by an inner surface of the outer chamber. The outer chamber may include or be formed from a thermal regulating material, while the inner chamber includes an at least partially hollow portion for receiving a container. A biological sample, frozen or otherwise, may be inserted into the inner chamber. The heater may then be activated, and begin transmitting heat to the thermal regulating material in the outer chamber. The heat received by the thermal regulating material will cause the thermal regulating material to heat and to begin to melt while maintaining a constant temperature. The heat may then be transmitted from the thermal regulating material to the inner chamber, causing the biological sample to warm. Samples which are frozen may both be thawed out and heated.

According to one aspect of the invention, a method for uniformly heating a biological sample is provided. A heater is engaged with an outer surface of a device having an outer chamber and an inner chamber defined by an inner surface of the outer chamber. The outer chamber may include or be formed from a thermal regulating material, while the inner chamber includes an at least partially hollow portion for receiving a container. A container holding a liquid in close intimate contact with a biological sample, frozen or otherwise, may be inserted into the inner chamber. The heater may then be activated, and begin transmitting heat to the thermal regulating material in the outer chamber. The heat received by the thermal regulating material will cause the thermal regulating material to heat and to begin to melt while maintaining a constant temperature. The heat may then be transmitted from the thermal regulating material to the liquid, and from the liquid to the biological sample. Frozen biological samples will both thaw and heat.

Additional features, advantages, and embodiments of the invention may be set forth or apparent from consideration of the detailed description and drawings. Moreover, it is to be understood that the foregoing summary of the invention and the following detailed description, drawings and attachment are exemplary and intended to provide further explanation without limiting the scope of the invention as claimed.

BRIEF DESCRIPTION OF THE DRAWINGS

The accompanying drawings, which are included to provide a further understanding of the disclosure, and are incorporated in and constitute a part of this specification, illustrate embodiments of the disclosure and together with the detailed description serve to explain the principles of the disclosure. No attempt is made to show structural details of the disclosure in more detail than may be necessary for a fundamental understanding of the disclosure and the various ways in which it may be practiced. In the drawings:

FIG. 3 of the drawings is a top perspective view of an embodiment of the invention;

FIG. 4 of the drawings is a front view of a removable container utilized in multiple embodiments of the invention;

FIG. 5 of the drawings is a cutaway of a top perspective view of an embodiment of the invention.

FIG. 8 shows a front view of an embodiment of the invention;

FIG. 9 shows a top view of an embodiment of the invention;

FIG. 10 shows an exemplary characteristic curve of the invention.

DETAILED DESCRIPTION OF THE DRAWINGS

Figure 1:
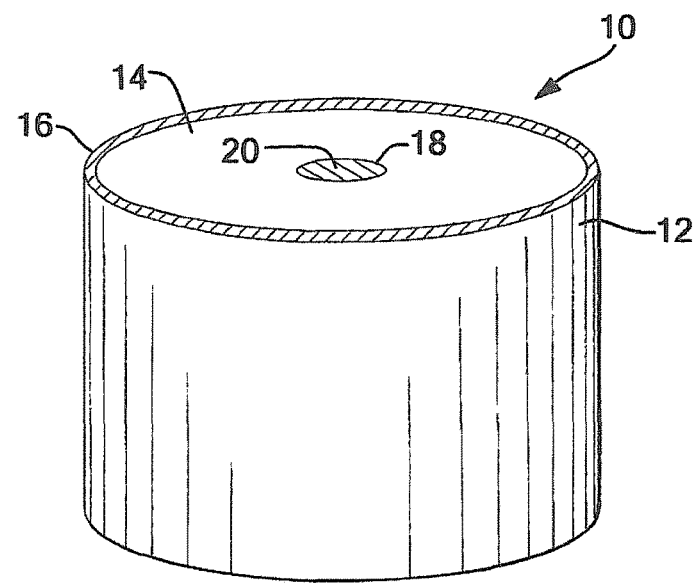
FIG. 1 of the drawings is top perspective view of an embodiment of the invention.

The present, disclosure and the various features and advantageous details thereof are explained more fully with reference to the non-limiting embodiments and examples that are described and/or illustrated in the accompanying drawings and detailed in the following description. It should be noted that the features illustrated in the drawings are not drawn to scale, and features of one embodiment may be employed with other embodiments, as the skilled artisan would recognize, even if not explicitly stated herein. Descriptions of well-known components and processing techniques may be omitted so as to not unnecessarily obscure the embodiments of the disclosure. The examples used herein are intended merely to facilitate an understanding of ways in which the invention may be practiced and to further enable those of skill in the art to practice the examples of the disclosure. Accordingly, the examples and embodiments herein should not be construed as limiting the scope of the invention.

The present invention is directed to a device for warming of biological samples, frozen or otherwise, by providing a substantially constant temperature to a biological sample at a temperature below that which will damage the biological sample. In order to provide uniform heating over the entire sample, the device may include a liquid, or may have a portion which is formable or malleable to substantially adhere to the entire surface of the same for thawing. It is important that the heat transfer be substantially uniform and be applied over the entire surface of the sample in order to provide uniform thawing and/or warming.

FIG. 1 shows a front perspective view of an embodiment of a device for warming biological samples as contemplated by the invention. Device 10 includes heater 12 and an outer chamber 14 which includes an outer surface 16 and an inner surface 18. Inner surface 18 defines a reservoir or biological sample receiving region 20 which extends vertically through at least a portion of outer chamber 14. In the devices discussed herein common reference numbers will refer to substantially similar elements across the different embodiments, like, for example, outer chamber 14, 114, 214. Except as discussed, the characteristics discussed with respect to any single embodiment will be substantially similar to the other embodiment whether directly referenced or not.

Heater 12 operatively contacts, is coupled to, or otherwise engages outer chamber 14 at outer surface 16, and may partially or fully surround and enclose the outer chamber. The heater may be any device capable of coupling to the outer chamber and producing and imparting heat thereon. For example, heater 12 may be a heater which produces heat as the result of an exothermic reaction, like for example, an oxygen activated heater. When an oxygen activated heater is used, the heater may include a pull tab 122 (see FIG. 2) or a similar element to activate the heater. Alternatively, heater 12 may be, for example, an electric wrap or sleeve which is battery powered or includes a power cord for connecting to a power source. Of course, as would be recognized by those having ordinary skill in the art, other types of heaters are also contemplated.

In addition, it is also contemplated by the invention that the device may not include an integrated or associated heater. As seen in FIG. 3, for example, device 210 includes outer chamber 214 having outer surface 216 and inner surface 218 which defines reservoir or biological sample receiving region 220 and is constructed in substantially the same manner as device 10 in FIG. 1. When a heater is not initially provided (or integrated or engaged with the outer chamber as part of the overall construction of the device), in order to operate the device a user may physically couple a heater to outer surface 216 of outer chamber 214 in order to utilize and operate the device.

To insure uniform heating of a biological sample at a substantially constant temperature, outer chamber 14 may include, or be substantially constructed from, a thermal regulating material. The thermal regulating material may form the outer chamber 14 itself, or alternatively be housed within a heat conductive housing or casing which forms at least the inner and outer surfaces of outer chamber 14. The heat imparted to the outer chamber will be through outer surface 16 and transmitted by the thermal regulating material to a biological sample received in biological sample receiving region 20 through inner surface 18.

In order to insure the relatively constant predetermined temperature throughout the thawing and/or warming process, the thermal regulating material should be a solid material which has a melting point less than that which will cause damage to a deposited biological material once heater 12 or some other engaged heater is activated and providing heat to the outer chamber. While undergoing the phase change from solid to liquid, the temperature of the thermal regulating material will remain substantially constant proximate the melting point temperature, until all of the solid material has melted and the thermal regulating material has completely liquefied. Additionally, after the active heating phase has ended the temperature of the thermal regulating material will remain substantially constant while the thermal regulating material re-solidifies. In this sense, the material for use in a particular device 10 may be chosen in order to provide a desired output temperature based on the speed with which the sample is to be thawed and the temperature at which a particular sample will be damaged. As the thermal regulating material re-solidifies, it can transfer latent heat, also at a substantially constant temperature so long as the phase change is ongoing, to the inner surface to the biological receiving region and the biological sample and any intermediaries deposited therein, like for example a container and/or surrounding liquid.

Materials which may be used for the thermal regulating material include, but are not limited to, palm oil, palm kernel oil, coconut oil, hydrogenated palm oil, hydrogenated palm kernel oil, hydrogenated coconut oil, hydrogenated soybean oil, hydrogenated cottonseed oil, a distearate of polyethylene glycol, or mixtures thereof. The thermal regulator may also contain 1-hexadecanol. Any number of materials may be used, depending on what the desired temperature the sample is to be heated to. For example, if the desired temperature of the sample is 37° C., a glycol chain of approximately 400 g/mol or palm oil may be utilized. The resulting latent heat of the material used for the thermal regulating material should be at least 20 cal/g, and more preferably will be 30 cal/g or even 40 cal/g in order to insure quick and complete thawing. In addition to the type of material used, as will be discussed further herein, the amount of material used may also control the temperature provided to the biological receiving region and ultimately any sample therein.

Biological sample receiving region 20 is configured to operatively accept a biological sample, which may be a frozen biological sample, and facilitate close and intimate contact between the sample and inner surface 18 of outer chamber 14 either directly or indirectly through the use of an intermediary like an inner liquid or the like. It is contemplated that the biological sample receiving region have at least one permanently or selectively opened portion and have a substantially hollow portion extending along at least a portion of the length of the outer chamber to receive and hold any biological samples, intermediaries, liquids, sleeves, and/or containers used in the thawing and/or warming process. The biological sample receiving region may be shaped as desired, and as discussed herein, may be formable or malleable to provide for a particular shape or configuration to match a sample or container. When an intermediary like a liquid is utilized, intimate contact with the surface of the sample or a container housing the sample is insured so that heat is transferred uniformly over the entire surface of the biological sample or a container used to house the biological sample. If a liquid is used, the liquid should have a freezing temperature similar to or lower than that of the sample so as to prevent or minimize freezing of the liquid once the sample is deposited or submerged.

Figure 6:
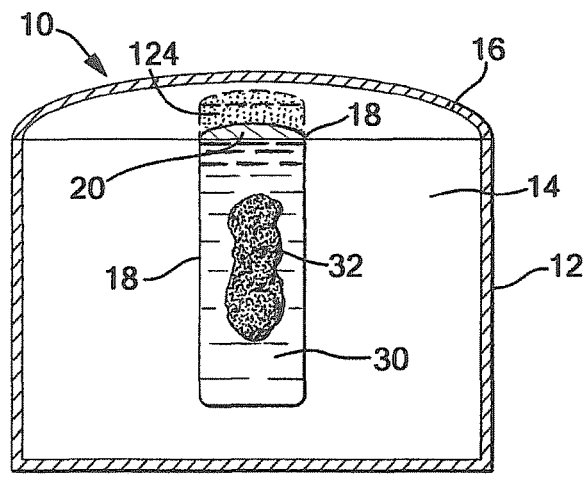
FIG. 6 of the drawings is a cutaway of a top perspective view of an embodiment of the invention.
Figure 7:
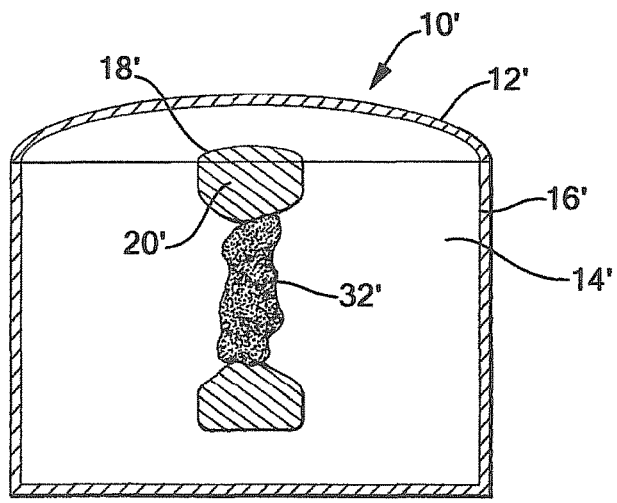
FIG. 7 of the drawings is a cutaway of a top perspective view of an embodiment of the invention.

Any liquid and/or biological samples which are to be deposited into biological receiving region 20 may be directly deposited therein. In embodiments where the sample is to be deposited directly into a liquid contained within the biological sample receiving region, for example, the receiving region may be at least selectively openable and closable at one or both ends in order to prevent the liquid from escaping the biological sample receiving region. Preferably, as seen in FIG. 5, which is a front cut away of FIGS. 1 and 2, for example, at least one end of the biological receiving region will be permanently sealed or closed in order to better prevent any leakage of liquid from region 34 which may include a liquid surrounding container 124 within biological sample receiving region 20. If the sample and/or a container holding the sample is to be deposited in the receiving region without liquid in the receiving, like for example as shown in FIGS. 6 and 7, which are also front cut aways of FIGS. 1 and 2, the receiving region may be matched to a particular vial or container and/or one or both ends of the receiving regions may be selectively or permanently open.

Figure 2:
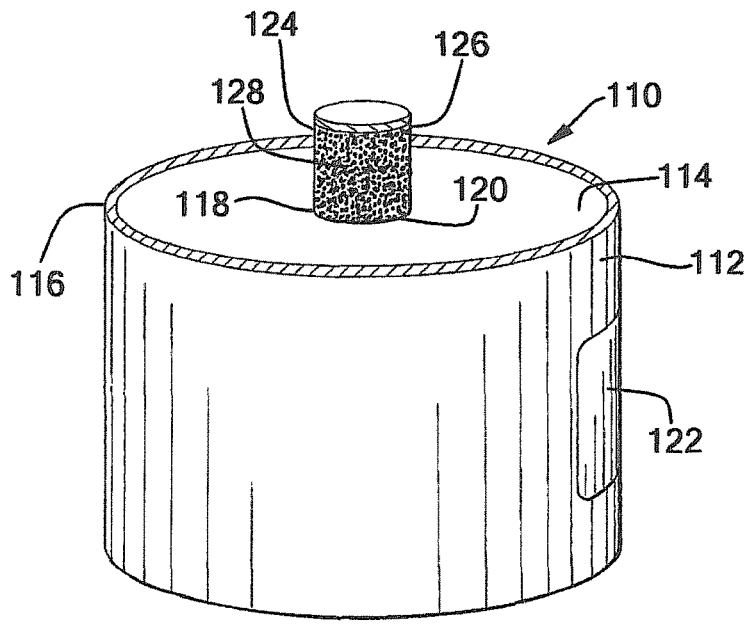
FIG. 2 of the drawings is a top perspective view of an embodiment of the invention.

Device 10 or 110 may include a container, which may be removable, like for example container 124 shown in FIGS. 2 and 4. Container 124 includes an outer surface 126 which is placed in direct, which may be placed in direct, operative contact with inner surface 18, 118 when deposited into biological sample receiving region 20, 120 so that heat is transferred directly and efficiently from inner surface 18, 118 to container 124 (as seen in FIG. 6 for example). Alternatively, when a liquid is deposited within a region or portion of the biological sample receiving region 20, 120 (like for example, area 34 in biological sample receiving region 20 in FIG. 5), the liquid may be placed in close and intimate contact with the liquid rather than the inner surface 18, 118.

Container 124 also includes an inner surface or region 128 which then holds a biological sample and may hold any further liquid used as an intermediary therein. The inner surface will operatively contact either the biological sample or any liquid intermediary therein to facilitate the heat transfer from the outer chamber to the biological sample. Insofar as the inner and outer surfaces of the container will act as a conduit for heat, the container should preferably be manufactured from a material having an acceptable coefficient of heat transfer—acceptable being a coefficient which allows enough heat to pass through without allowing so much as to damage any sample contained in the container, or to damage the container itself. For example, the container may be constructed from glass, plastic, or ceramic and may be a glass vial or test tube.

An example of a removable container holding an additional liquid and biological sample can be seen in FIG. 4. As seen in FIG. 4, container 124 has outer surface 126, inner region/surface 128 and holds liquid 130 in direct, operative, and intimate contact with both inner surface 128 and biological sample 132. Sleeve 125 may be included to surround container 124 to protect the vial when a liquid is used in an associated biological sample receiving region. As can be seen in FIG. 5, which is a front cutaway of FIGS. 1 and 2, the outer surface of container 124 (shown in phantom in FIG. 5), will directly contact the inner surface 18 or 118 of outer chamber 14 or 114. When no container is used, as seen in FIG. 5, liquid 30 may be placed directly into biological sample receiving region 20 and biological sample 32 deposited into liquid 30. It should be understood that in embodiments with no heater provided with the device, like for example FIG. 3, the interior of the device will remain substantially the same (heater 12 surrounding outer surface 16 will simple be removed and not provided).

FIG. 7 shows an example of a device 10' which may be utilized without any liquid, i.e. a device which allows for the biological sample or a biological sample within a container to be deposited directly into the biological sample receiving region so that the inner surface of the outer chamber contacts the sample directly. As seen in FIG. 7, device 10' includes heater 12' (again, optional, see FIG. 3), an outer chamber 14' which has outer surface 16' operatively connected to heater 12' and inner surface 18' which defines biological receiving region 20'. Biological sample 32' is deposited directly in the biological sample receiving region 20' and the inner surface 18' is formed or de-formed to intimately and directly contact the entire outer surface of biological sample 32' directly to provide for direct heating of the sample. In such embodiments, in order to insure uniform heating over the entire surface of the sample, outer chamber 14' may be formable or malleable in order to form around the sample. For example, outer chamber 14' may be constructed using a material like wax which will allow for manipulation and formation around the sample. Though not shown in FIG. 6, it is contemplated that a container can be used within the biological sample receiving region as shown in FIGS. 2 and 6 in phantom, for example.

In operation, the device works as follows. Device 10, 110, 210 will have a biological sample 32, or a container 124 housing a biological sample 132, deposited within biological sample receiving region 20, 120, 220, along with any liquid 30, 130 utilized during the thawing and/or warming process. Heater 12, 112, or in the case of FIG. 3 an external heater attached to device 210, will be activated and begin transmitting heating to outer surface 16, 116, 216 of outer chamber 14, 114, 214. Once the heater is activated, the thermal regulating material either forming or within the outer chamber will begin to heat and undergo a phase change, and begin transmitting heat through inner surface 18, 118, 218 to the biological sample receiving region. The constant temperature provided by the thermal regulating material will then heat any container, liquid, or the biological sample directly and be used to thaw and/or warm the biological sample. Since the thermal regulating material is undergoing a phase change at a substantially constant temperature (within a range of ±2° C.), the temperature of heat being provided to the receiving region will remain substantially constant and can be set at an amount which will thaw and/or warm the sample without damaging it. Preferably, the thermal regulating material is scaled and constructed so that no more than 90% of the thermal regulating material is melted when the sample is completely thawed and/or warmed. Aiming for 90% reduces any wasted, un-melted material, while providing some amount of protection for the sample so that the temperature imparted on the biological sample receiving region does not exceed a threshold which will damage the sample. For systems where the intent is to merely thaw the biological sample, the thermal regulating material may not melt at all but may serve as a safety feature to prevent unintended warming to temperatures above the melting temperature of the thermal regulator.

As discussed herein, any liquid which is used should also be selected based upon the liquid characteristics. Most important, the liquid should have a freezing point near to or lower than the temperature of any sample, and a boiling point lower than the temperature provided by the thermal regulating material. For example, in operation, the liquid used may have a freezing point below −80° C. and a boiling point above 105° C. to prevent freezing and boiling.

In support of the above described method and structure of the device the following experiment was conducted.

A device used in the experiment can be seen in FIGS. 8 and 9. Device 300 includes a heater 302, an outer chamber 304 filled with a thermal regulator, and an inner chamber 306 filled with a liquid. For the purposes of this experiment, the thermal regulator deposited in the outer chamber was 20 g of polyethyleneglycol distearate ("PEG Distearate") and the liquid was 20 g of water. In order to allow for heater activation, device 300 was provided with external openings 308 which were formed in a pattern in order to allow air access to heater 302 to activate the heater. In this experiment, the heat source was selected to generate heat using a zinc-air reaction.

After heater activation, the temperature of the liquid in the inner chamber rose to 37° C. Once the liquid reached 37° C., two vials 310 and 312 each containing 1.3 mLs of a frozen aqueous solution and which had been chilled to −65° C., were placed into the heated water. Thermocouples in the vials and in the inner chamber were used to record the temperature of the liquid and the sample. 30° C. within the vials was reached within five minutes in the heated liquid. In addition, the thermal regulator successfully prevented temperatures from exceeding 37° C.

FIG. 10 shows a characteristic curve showing the resulting heating of the vials within the liquid. As seen in FIG. 10, the heating curve for vial 1 (310) and vial 2 (312) warm up quickly to approximately 30° C., i.e. within five minutes as discussed above, and then eventually levels off at approximately 37° C. as desired. The water bath liquid curve likewise cools, eventually leveling off at approximately 37° C., insuring that the vials and any contents therein are heated at the desired temperature.

The following table shows the melting points and latent heat of fusion for different thermoregulators which may be used in the device.

| Thermoregulator | Melting Point (° C.) | Latent Heat of Fusion (cal/g) |
|---|---|---|
| PEG Distearate | 35-37 | 20-40 |
| Cocoa Butter | 34-36 | 30-45 |
| Low MP Parrafin 19 or 20 | 32-38 | 60 |
| Hydrogenated Coconut Oil | 36-40 | 30-45 |

Depending on the desired heating temperature and the heat or time required to thaw a vial and its contents, different thermoregulators may be chosen to meet the requirements.

Though this invention has been discussed periodically throughout with respect to thawing frozen biological samples, it should be understood that the device and methods discussed herein may also be used to uniformly heat frozen or unfrozen or already thawed biological material. As defined herein, the device and method is for uniformly heating a biological sample, which may or may not include thawing a frozen biological sample. For example, in some situations it may be desirable to heat a bag of blood plasma which has been refrigerated at a temperature of 4° C. to body temperature, approximately 37° C. Whether it is chilled blood or some other biological material which has just been chilled or is at room temperature, for example, the same device and method may be utilized to accomplish such heating, with the only difference being the material being already thawed. In order to facilitate uniform heating of such a biological sample, a thermal capacitor may be attached to the sample and any vessel containing the sample.

Additional features, advantages, and embodiments of the invention may be set forth or apparent from consideration of the detailed description and drawings. Moreover, it is to be understood that the foregoing summary of the invention and the associated detailed description and drawings are exemplary and intended to provide further explanation without limiting the scope of the invention as claimed.

What is claimed is:

1. A device for uniformly warming biological samples comprising:
   a heater;
   an outer chamber comprising a thermal regulating material, wherein the outer chamber includes an outer surface and an inner surface, and, wherein the heater is in operative contact with at least a portion of the outer surface of the outer chamber;
   a biological sample receiving region defined by the inner surface of the outer chamber, wherein the biological sample receiving region operatively accepts a biological sample,
   wherein the thermal regulating material is a solid material that undergoes a phase change to a liquid state upon exposure to a predetermined temperature imparted to it from the heater and the thermal regulating material obtains and maintains a substantially constant predetermined temperature when heat is imparted to the outer chamber at least while undergoing the phase change.

2. The device according to claim 1, wherein the temperature of the thermal regulating material remains substantially constant while the heat imparted to it from the heater induces at least a partial phase change of the thermal regulating material from its solid state to its liquid state.

3. The device according to claim 2, wherein the thermal regulating material maintains a constant temperature in the biological receiving region at least while undergoing a phase change from solid to liquid.

4. The device according to claim 3, wherein the thermal regulating material imparts heat to the biological sample receiving region at a temperature that will warm the biological sample without causing damage thereto.

5. The device according to claim 1 further including a container positioned within the biological sample receiving region, wherein the container comprises an outer surface having at least a portion surrounded by and in operative contact with one or more of a liquid or the inner surface of the outer chamber, the container including an inner surface, and, an interior region for operative positioning of a biological sample.

6. The device according to claim 5 wherein the container includes a sleeve within the biological sample receiving region, the sleeve housing the container and being in close and intimate contact with a liquid contained in the biological sample receiving region.

7. The device according to claim 5, wherein the container is fabricated from a material that allows for effective heat transfer from the thermal regulating material so as to enable heating, and, in turn, warming of the biological sample without causing damage thereto.

8. The device according to claim 7, wherein the container comprises a glass or plastic vial.

9. The device according to claim 1, wherein the heater comprises a heater that produces heat from an exothermic reaction.

10. The device according to claim 9, wherein the heater comprises an oxygen activated heater.

11. The device according to claim 1, wherein the thermal regulating material includes one or more from the group comprising: palm oil, palm kernel oil, coconut oil, hydrogenated palm oil, hydrogenated palm kernel oil, hydrogenated coconut oil, hydrogenated soybean oil, hydrogenated cottonseed oil, a distearate of polyethylene glycol, and 1-hexadecanol.

12. The device according to claim 1 wherein the thermal regulating material has a melting point of approximately 37° C.

13. The device according to claim 1 wherein the latent heat of fusion of the thermal regulating material is at least 20 cal/g.

14. The device according to claim 13 wherein the latent heat of fusion of the thermal regulating material is at least 30 cal/g.

15. The device according to claim 14 wherein the latent heat of fusion of the thermal regulating material is at least 40 cal/g.

16. The device according to claim 1 wherein the biological sample receiving region includes a liquid which surrounds and is in intimate contact with a received biological sample, the liquid having a freezing point near to or below that of the received biological sample.

17. The device of claim 1 wherein the heater is a removable patch.

18. A device for uniformly warming biological samples comprising:
   a heater;
   an outer chamber comprising a thermal regulating material, wherein the outer chamber includes an outer surface and an inner surface, and, wherein the heater is in operative contact with at least a portion of the outer surface of the outer chamber;
   a biological sample receiving region completely surround by the outer chamber and is defined by the inner surface of the outer chamber, wherein the biological sample receiving region operatively accepts a biological sample, wherein the thermal regulating material is a solid material that undergoes a phase change to a liquid state upon exposure to a predetermined temperature imparted to it from the heater and the thermal regulating material obtains and maintains a substantially constant predetermined temperature when heat is imparted to the outer chamber at least while undergoing the phase change, and transmits heat at substantially the substantially constant predetermined temperature to the biological sample receiving region through the inner surface.

19. A device for uniformly warming biological samples comprising:

a heater;

an outer chamber comprising a casing forming an outer surface and an inner surface, and a thermal regulating material disposed between the outer surface and the inner surface of the casing, wherein the thermal regulating material is in thermal contact with both the outer surface and the inner surface and is a solid material which undergoes a phase change to a liquid state upon exposure to a predetermined temperature imparted to it;

a biological sample receiving region defined by the inner surface of the outer chamber, the biological sample receiving region being in thermal contact with the thermal regulating material through the inner surface, wherein the thermal regulating material obtains and maintains a substantially constant predetermined temperature when heat is imparted to the outer chamber, at least while undergoing the phase change, and transmits heat at substantially the substantially constant predetermined temperature to the biological sample receiving region through the inner surface.

20. The device according to claim 19, wherein the thermal regulating material and the inner surface radially surround the biological sample receiving region.

* * * * *